United States Patent
Au et al.

(10) Patent No.: US 10,321,900 B2
(45) Date of Patent: Jun. 18, 2019

(54) OPERATING SELF-ANTAGONISTIC DRIVES OF MEDICAL INSTRUMENTS

(71) Applicant: Intuitive Surgical Operations, Inc., Sunnyvale, CA (US)

(72) Inventors: Samuel Kwok Wai Au, Mountain View, CA (US); Stephen J. Blumenkranz, Los Altos Hills, CA (US); Giuseppe Maria Prisco, Calci (IT)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 15/913,602

(22) Filed: Mar. 6, 2018

(65) Prior Publication Data

US 2018/0193007 A1  Jul. 12, 2018

Related U.S. Application Data

(62) Division of application No. 14/068,127, filed on Oct. 31, 2013, now Pat. No. 9,931,106.

(60) Provisional application No. 61/721,988, filed on Nov. 2, 2012.

(51) Int. Cl.
*A61B 17/00* (2006.01)
*A61B 34/00* (2016.01)
*A61B 34/30* (2016.01)

(52) U.S. Cl.
CPC ............ *A61B 17/00* (2013.01); *A61B 34/30* (2016.02); *A61B 34/71* (2016.02); *A61B 2034/715* (2016.02)

(58) Field of Classification Search
CPC .......... A61B 17/00; A61B 34/30; A61B 34/71; A61B 2034/715
USPC .............................................................. 606/1
See application file for complete search history.

(56) References Cited

U.S. PATENT DOCUMENTS

| | | |
|---|---|---|
| 4,688,555 A | 8/1987 | Wardle |
| 4,865,376 A | 9/1989 | Leaver et al. |
| 5,792,135 A | 8/1998 | Madhani et al. |
| 2002/0165485 A1 | 11/2002 | Simpson et al. |
| 2005/0228440 A1 | 10/2005 | Brock et al. |
| 2009/0088774 A1 | 4/2009 | Swarup et al. |
| 2009/0112230 A1 | 4/2009 | Jinno |
| 2010/0082041 A1 | 4/2010 | Prisco |
| 2010/0170519 A1 | 7/2010 | Romo et al. |
| 2012/0277762 A1 | 11/2012 | Lathrop et al. |

(Continued)

FOREIGN PATENT DOCUMENTS

| | | |
|---|---|---|
| EP | 2415418 A1 | 2/2012 |
| JP | S61236491 A | 10/1986 |

(Continued)

OTHER PUBLICATIONS

Extended European Search Report for Application No. 13850483.2, dated Jun. 1, 2016, 7 pages.

(Continued)

*Primary Examiner* — Aaron F Roane
(74) *Attorney, Agent, or Firm* — Fish & Richardson P.C.

(57) ABSTRACT

A medical instrument including a shaft and an actuated structure mounted at a distal end of the shaft can employ a pair of tendons connected to the actuated structure, extending down the shaft, and respectively wound around a capstan in opposite directions. A passive preload system may maintain minimum tensions in the tendons.

13 Claims, 4 Drawing Sheets

(56) References Cited

U.S. PATENT DOCUMENTS

2014/0128849 A1  5/2014  Au et al.

FOREIGN PATENT DOCUMENTS

JP          S62254726 A    11/1987
WO    WO-2010039387 A1   4/2010

OTHER PUBLICATIONS

International Search Report and Written Opinion for Application No. PCT/US2013/067680, dated Feb. 6, 2014, 15 pages.
Office Action dated Dec. 27, 2016 for Chinese Application No. 201380056643.1 filed Oct. 31, 2013, 18 pages.
Office Action dated Aug. 29, 2017 for Japanese Application No. 2015540778 filed Oct. 31, 2013, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

OPERATING SELF-ANTAGONISTIC DRIVES OF MEDICAL INSTRUMENTS

CROSS-REFERENCE TO RELATED APPLICATIONS

This patent document is a divisional of U.S. patent application Ser. No. 14/068,127, filed Oct. 31, 2013, which claims benefit of the earlier filing date of U.S. provisional patent application No. 61/721,988, filed Nov. 2, 2012, both of which are hereby incorporated by reference in its entirety.

BACKGROUND

Instruments for minimally invasive medical procedures can be directly manipulated manually or can be operated with computer control or computer assistance. However, computer manipulation of a medical instrument often places strict mechanical requirements on the medical instrument. In particular, the mechanical systems of a robotic medical instrument may need to have a tightly controlled response to actuator operation, so that a computerized control system can calculate actuator movement that will achieve a precise movement of the instrument. Actuator controlled medical instruments may also need docking structures that engage electronically controlled actuators. For these reasons and others, medical instruments that are suitable for computer assisted operation tend to be cumbersome or difficult to use manually.

FIG. 1 schematically illustrates a medical instrument that may be used in a robotic system for a minimally invasive medical procedure. (As used herein, the terms "robot" or "robotically" and the like include teleoperation or telerobotic aspects.) Instrument 100 includes a tool or end effector 110 at a distal end of a shaft 120. End effector 110 includes jaws 112 and 114 that are rotatably mounted. Jaw 112 is connected to a first pair of tendons 121 and 122, and jaw 114 is connected to a second pair of tendons 123 and 124. Additional tendons (not shown) may be connected in instrument 100 to a wrist mechanism or joints (not shown) that provide additional degrees of freedom for positioning and orienting end effector 110.

Tendons 121, 122, 123, and 124 apply forces and torques to jaws 112 and 114 when pulled by a backend mechanism 130 attached to the proximal end of shaft 120. Backend mechanism 130 may act as a transmission that converts the rotation of drive motors (not shown) into movement of tendons 121, 122, 123, and 124 and end effector 110. As shown, backend mechanism 130 includes one capstan 131, 132, 133, or 134 per tendon 121, 122, 123, or 124, and the proximal ends of tendons 121, 122, 123, and 124 respectively wrap around capstans 131, 132, 133, and 134 and then attach to preload systems 135, 136, 137, and 138. Preload systems 135, 136, 137, and 138 can be biased, e.g., include stretched springs, so that non-zero forces are applied to the proximal ends of respective tendons 121, 122, 123, and 124 through the full range of motion of end effector 110. With this configuration, when capstans 131, 132, 133, and 134 are free to rotate, the corresponding preload system 135, 136, 137, or 138 provides tension and avoids slack in tendon 121, 122, 123, and 124.

End effector 110 can be operated using drive motors that are under the active control of software executed in a controlled system that interprets human input (e.g., through master control input in a master-slave servo control system). In particular, four drive motors, which are provided in a docking port of a control system (not shown), can be respectively coupled to rotate capstans 131, 132, 133, and 134. Backend mechanism 130 may dock with an interface of the control system including motors or other actuators. When backend mechanism 130 is removed from the dock, handheld operation of backend mechanism 130 may be difficult particularly because of the shape of backend mechanism 130 and the accessibility of capstans 131, 132, 133, and 134 and because control of each degree of freedom of end effector 110 involves using two capstans, e.g., capstans 131 and 132 or 133 and 134.

SUMMARY

In accordance with an aspect of the invention, a medical instrument including a shaft and an actuated structure mounted at a distal end of the shaft can employ a pair of tendons connected to the actuated structure, extending down the shaft, and respectively wound around a capstan in opposite directions to provide a self-antagonistic drive system. A preload system may be coupled to maintain minimum tensions in the tendons.

One specific embodiment of the invention is a medical instrument including an actuated structure mounted at a distal end of a shaft in a manner that permits movement of the actuated structure relative to the shaft. Two tendons, which may be opposite ends of a continuous cable or similar structure, may connect to the actuated structure and extend down the shaft. A portion of one tendon may be wound in a first direction around a capstan at a proximal end of the shaft, and a portion of the other tendon can be wound around the capstan in a second direction that is opposite of the first direction. A passive preload system may be coupled to maintain tension in the tendons.

Another specific embodiment of the invention is a method for operating an instrument that includes an actuated structure mounted at a distal end of a shaft. The method includes driving rotation of a capstan that has a first tendon wrapped around the capstan in a first direction and a second tendon wrapped around the capstan in second direction that is opposite to the first direction. Distal portions of the first and second tendons extend along the shaft and engage the actuated structure. The method further includes passively controlling tension in proximal portions of the first and second tendons that extend from the capstan.

BRIEF DESCRIPTION OF THE DRAWINGS

Use of the same reference symbols in different figures indicates similar or identical items.

DETAILED DESCRIPTION

A drive system for a medical instrument can employ a single motor driven capstan on which two actuating tendons are oppositely wound for self-antagonistic drive of an actuated structure such as an end effector. In general, an antagonistic drive can actuate a degree of freedom using two drive cables or tendons respectively connected to pull in opposing directions. With one type of antagonistic drive, the two tendons connect to two independent drive motors or actuators that are respectively associated with opposing directions of a single degree of freedom. However, with self-antagonistic actuation as described herein, the two cables associated with opposite directions of a degree of freedom can connect to the same drive motor or actuator. As a result, a self-antagonistic drive system can employ one motor or actuator per degree of freedom of an actuated structure, allowing the drive system to be simpler, lower cost, and more compact than a drive system using one motor or actuator per actuating tendon. Further, a self-antagonistic drive system can be suitable for both handheld and robotic operation. One or more preload systems can maintain tension in the actuating tendons, even when drive motors or actuators are off, which also facilitates in allowing the handheld or robotic operation. In different configurations, the drive systems can be connected to proximal ends of the actuating tendons, directly or through pulley systems, or can be connected to a slide mounted motor or capstan.

Figure 2:
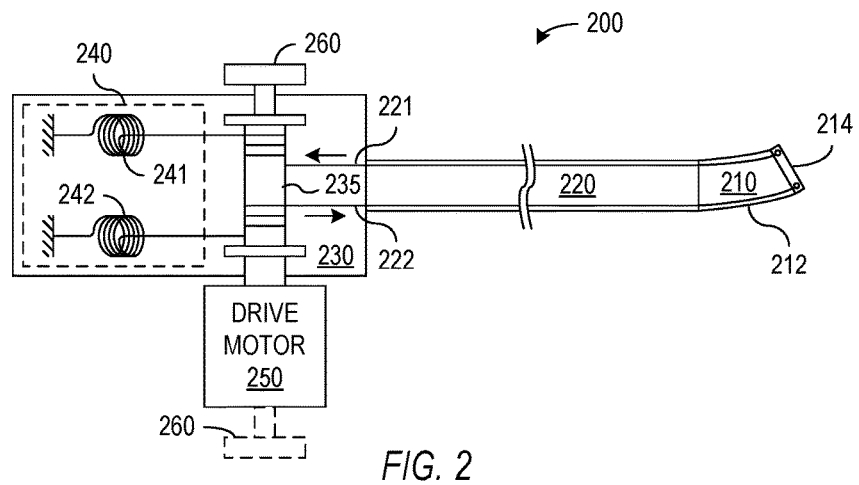
FIG. 2 shows a medical instrument with a control system using a single capstan with oppositely wound actuating tendons respectively connected to independent preload systems.

FIG. 2 schematically illustrates a medical instrument 200 in accordance with an embodiment of the invention. Instrument 200 includes an actuated structure or steering section 210 at a distal end of a main tube 220, which is connected to a backend mechanism 230. Steering section 210 in the illustrated embodiment includes flexible tubing 212 and an actuation ring 214. Steering section 210 may, for example, include tubular vertebrae that are interconnected by joints or alternatively a tube of an elastic material such as Nitinol having kerfs cut to create flexures. Steering section 210 may additionally include sheathing that covers the joints or flexures. Ring 214 may be a rigid structure having actuating tendons 221 and 222 coupled to opposite edges of ring 214, so that pulling on tendon 221 or 222 tends to bend flexible tubing 212 in one direction or the opposite direction of one degree of freedom of motion of ring 214. In a typical embodiment, a second pair of tendons (not shown) may be connected to actuation ring 214 for actuated movement in another degree of freedom for movement of ring 214. Many other alternative embodiments of steering section 210 are possible. For example, steering section 210 could include multiple independently actuated joints, and tendons 221 and 222 may be employed to actuate one of those joints. Also, tendons 221 and 222 may be opposite ends of a continuous structure such as a cable that winds through ring 214 or around a particular joint in steering section 214.

Tube 220 may be a rigid or flexible tube but is generally less flexible than steering section 210. In particular, main tube 220 may be sufficiently flexible to follow the path of a natural lumen. However, for steering of main tube 220, a backend mechanism 230 can apply different forces or tensions to tendons 221 and 222. The desired result of the applied forces is bending of steering section 210 in a direction of the steering and minimal bending of tube 220. To achieve this goal, main tube 220 may be more rigid than steering section 210, or each tendon 221 or 222 may be a Bowden cable, e.g., a pull wire enclosed in a housing, which will minimize the bending of tube 220. Tendons 221 and 222 can otherwise be stranded cables, wires, rods, or tubes made of metal, a polymer, or other material. In an exemplary embodiment, tendons 221 and 222 may include connected portions of different construction, e.g., stranded cable that are fused to tubes. For example, the stranded cable may be used where significant bending or flexing of the tendons 221 and 222 is expected, and the more-rigid tubes may be used elsewhere to reduce stretching of tendons 221 and 222.

Figure 1:
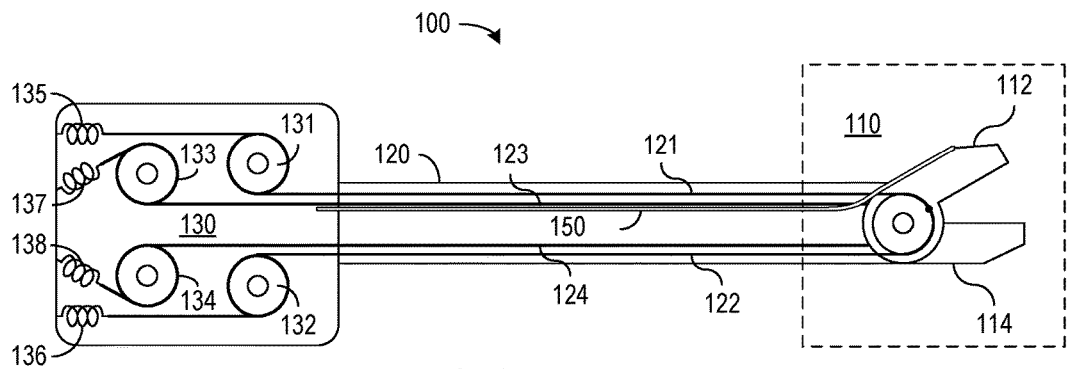
FIG. 1 schematically illustrates a known medical instrument that can be robotically controlled during a minimally invasive medical procedure.

FIG. 2 illustrates an example instrument in which actuating tendons 221 and 222 attach to steering section 210, but alternatively actuating tendons 221 and 222 could be used to operate other types of actuated structures such as a jaw as shown in FIG. 1, another type of jointed structure, or any other mechanisms that permits movement of mechanical members of a medical instrument. For example, tendons 221 and 222 could drive a pivot, planar, cylindrical, or spherical rolling joint or flexure that provides clockwise and counterclockwise rotational freedom to a jaw or other structure or drive a prismatic linear joint or slide that provides linear bi-directional freedom of motion to an actuated structure.

Backend mechanism 230 attaches to the proximal end of tube 220 and acts as a transmission that converts the rotation of a drive motor 250 into movement of or tension in actuating tendons 221 and 222. Backend mechanism 230 particularly manipulates tendons 221 and 222 to operate steering section 210. In the illustrated embodiment, backend mechanism 230 includes a capstan 235 around which portions of both actuating tendons 221 and 222 are wound in opposite directions. For example, tendon 221 may be wound around capstan 235 so that counterclockwise rotation of capstan 235 reels in more of tendon 221 from the side of tendon 221 leading to steering section 210, and tendon 222 may be wound around capstan 235 so that counterclockwise rotation of capstan 235 feeds out more of tendon 222 toward steering section 210. Movement of steering section 210 back and forth along one degree of freedom can thus be actuated through rotation of a single capstan 235.

Drive motor 250 is connected to rotate capstan 235, and in some implementations, capstan 235 is an extension of or is part of the shaft of motor 250. In some other implementations, drive motor 250 has a detachable connection to capstan, so that backend mechanism 230 may be separated from motor 250. Motor 250 may be under the robotic control based on human input (e.g., master control input in a master-slave servo control system) and software executed in a robotically controlled system. Additionally, a knob, lever, or other hand-operated manipulator 260 is coupled to capstan 235 or motor 250, and enables a user to manually operate instrument 200 through manual rotation of capstan 235. Instrument 200 may thus be used with or without motor 250 or knob 260 applying a torque to capstan 235.

In various embodiments, a preload system 240 can be employed to maintain minimum and equal tension in tendons 221 and 222, avoiding slack in tendons 221 and 222 as well as biased motion in steering section 210 even when neither motor 250 nor knob 260 applies a torque to capstan 235. Preload system 240 can be passive such that the applied tension does not need to respond to a control or feedback system. In other embodiments, preload system 240 can be actively controlled (e.g., applying tensioning when a minimum tendon tension or slack is detected or maintaining a predetermined tendon tension or tension range). In the embodiment of FIG. 2, proximal ends of tendons 221 and 222 extend from capstan 235 to preload system 240. In particular, each tendon 221 or 222 may wrap around capstan 235 for a set wrapping angle (that could be less than a full turn or include more than one turns) around capstan 235, and the proximal ends of tendons 221 and 222 extend past capstan 235 to connect to preload system 240. Tendons 221 and 222 are not required to be permanently attached to capstans 235 and thus may be able to slip relative to capstans 235, for example, when motor 250 or knob 260 turns in a direction that feeds tendon 221 or 222 out toward steering section 210. However, the wrap angle and the tension applied by preload system 240 are such that when motor 250 or knob 260 pulls in from the distal end of tendon 221 or 222, the torque applied by motor 250 or knob 260 controls the tension in the distal portion of that tendon 221 or 222.

Preload system 240 in the embodiment of FIG. 2 is implemented using springs 241 and 242 that may be anchored to a case or chassis of backend mechanism 230. Springs 241 and 242 may be biased, e.g., stretched, to apply non-zero and equal forces to respective tendons 221 and 222 throughout the range of motion of surgical instrument 200. With this configuration, when capstan 235 is free to rotate, springs 241 and 242 respectively pull on tendons 221 and 222 and control the tensions in tendon 221 and 222. Preload system 240 may thus prevent slack in tendons 221 and 222 by pulling in the required length of tendon 221 or 222. Further, preload system 240 applies an equal amount of tension on both tendons 221 and 222 to avoid biased motion in steering section 210 throughout the range of motion of surgical instrument 200.

Each spring 241 or 242 in preload system 240 more generally can be replaced with any structure or system that is able to apply a force to the free proximal end of a tendon 221 or 222 while allowing the required range of displacement of the proximal end of the tendon 221 or 222. Springs 241 and 242 can, for example, be linear coil springs, constant force springs, or use other spring elements, such as rotary coil springs, leaf springs or compliant members, such as bending beams, cantilever beams, or elastic bands. Springs 241 and 242 can be any type of compliant members, springs, or tension-applying systems, but the tension that spring 241 applies may ideally be equal to that applied by spring 242 throughout the range of motion of the instrument. Otherwise, the preload on each tendon may be unbalanced, creating biased motion at the steering section. Further, the spring elements or compliant members can work through extension or compression to apply force directly or indirectly to the end of the attached tendons. In addition, the spring elements or compliant members may be designed so that the force applied by spring 241 on tendon 221 is equal to the force applied by spring 242 on tendon 222 throughout the range of motion of the instrument 200. Other methods for applying the desired force, such as a system using weights or magnets, might alternatively be employed. In addition to the source of force, preload system 240 may include mechanical elements (not shown) that direct or control the magnitude of the force applied to the attached tendon, e.g., to apply a constant force throughout the range of motion of steering section 210.

Figure 3:
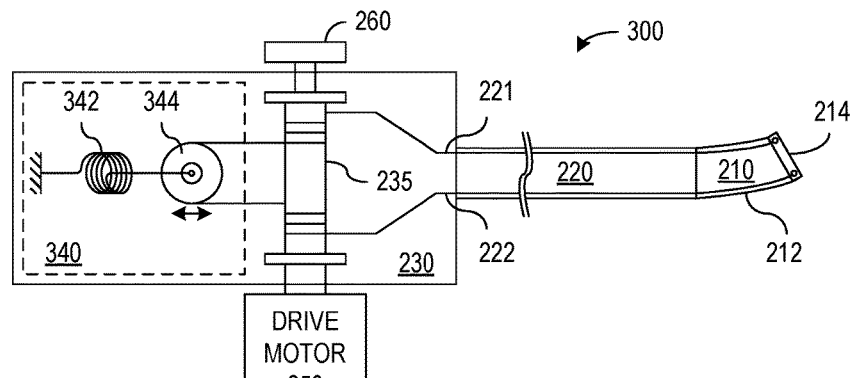
FIG. 3 shows a medical instrument with a control system using a single capstan with oppositely wound actuating tendons connected to a preload system including a spring loaded movable pulley.

FIG. 3 illustrates an example of an instrument 300 including a catheter having a main tube 220 and a steering section 210 that can be controlled using tendons 221 and 222 wound around a capstan 235 in a backend mechanism 230 as described above with reference to FIG. 2, but instrument 300 differs from instrument 200 by employing an alternative preload system 340. Preload system 340 includes a biased spring 342 attached to a pulley 344 having a slide mounting that permits pulley 344 to move toward or away from capstan 235. In preload system 340, the proximal ends of tendons 221 and 222 are connected together and looped around pulley 344. In operation, drive motor 250 or knob 260 can rotate capstan 235 to increase the tension in a distal portion of tendon 221 or 222 and cause steering section 210 to bend or move toward the higher tension tendon 221 or 222. At the same time, spring 342 allows pulley 344 to shift and rotate until the proximal ends of both tendons 221 and 222 carry tensions about equal to one half of the force that spring 342 applies to pulley 344. As described above, the tension in the distal portion of tendon 221 or 222 being pulled in will depend on the motor or manual torque applied to capstan 235, and the tension in distal portion of the tendon 222 or 221 being reeled out will be about the same as the tension at the proximal end. Preload system 340 can thus maintain non-zero and equal tensions in the proximal ends of tendons 221 and 222, avoiding slack in tendons 221 and 222.

Figure 4:
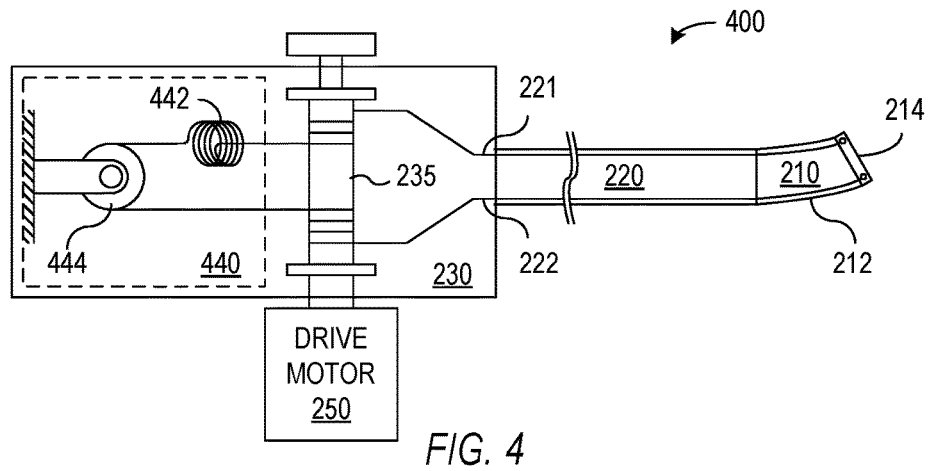
FIG. 4 shows a medical instrument with a control system using a single capstan with oppositely wound actuating tendons connected to a preload system including an in-line spring system and a fixed pulley.

FIG. 4 illustrates another example of an instrument 400 including a main tube 220 and a steering section 210 that can be controlled using tendons 221 and 222 wound around a capstan 235 in a backend mechanism 230 as described above with reference to FIG. 2, but instrument 400 includes another alternative preload system 440. Preload system 440 includes an in-line spring 442 and a fixed pulley 444. Fixed pulley 444 can be anchored to the walls, case, or chassis of backend mechanism 230. The proximal end of one tendon 221 or 222 connects to one end of spring 442, and the proximal end of the other tendon 222 or 221 connects to the other end of spring 442 after wrapping around fixed pulley 444. Spring 442 is biased, e.g., stretched, to apply equal tension to the proximal ends of tendons 221 and 222, and spring 442 has a sufficient range of motion to compensate for stretch that may occur in tendons 221 and 222 and axial compression of main tube 220 or steering section 210. Motor 250 or knob 260 can control a higher tension at the distal end of one tendon 221 or 222 as described above, while preload system 440 controls the minimum tension in both tendons 222 and 221.

Figure 5:
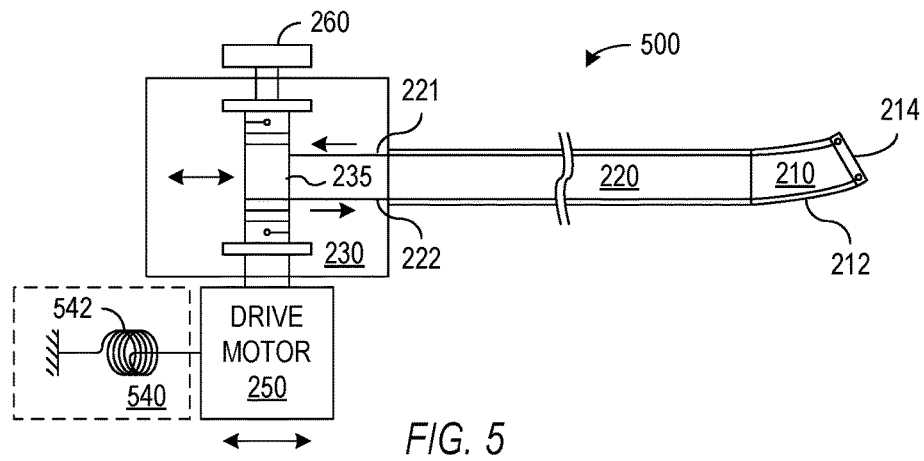
FIG. 5 shows a medical instrument with a control system using oppositely wound actuating tendons connected to a capstan in a spring-loaded, slide mounting.

FIG. 5 illustrates still another example of an instrument 500 also including a main tube 220 and a steering section 210 that can be controlled using tendons 221 and 222 wound around a capstan 235 in a backend mechanism 230 as described above with reference to FIG. 2. Instrument 500 includes a preload system 540 that spring loads capstan 235, instead of connecting directly to tendons 221 and 222. In FIG. 5, preload system 540 is coupled to drive motor 250, and drive motor 250 has a slide mounting that permits linear movement of motor 250 and capstan 235 in a direction perpendicular to the rotation axis of capstan 235. Alternatively, preload system 540 could couple to capstan 235 in another manner, e.g., to knob 260, bearings (not shown) of capstan 235, or to a slide mounting (not shown) of capstan 235. In the embodiment of FIG. 5, the proximal ends of tendons 221 and 222 can be attached to or fixed on capstan 235.

Figure 6:
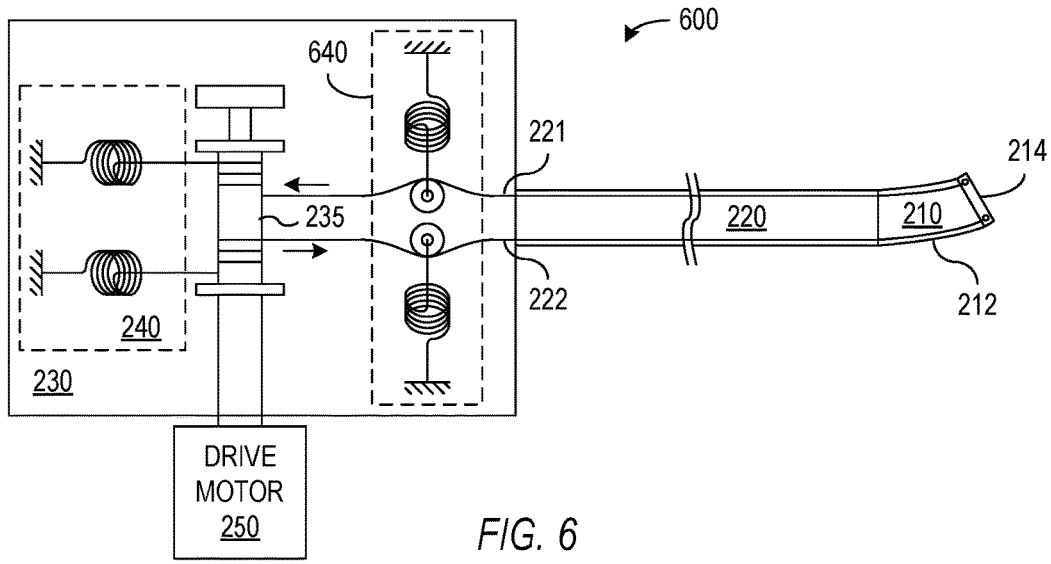
FIG. 6 shows a medical instrument with a control system using a single capstan with oppositely wound actuating tendons respectively connected to independent preload systems and additional take-up pulleys between the capstan and an actuated structure.

FIG. 6 illustrates yet another example of an instrument 600 also including a main tube 220 and a steering section 210 that can be controlled using tendons 221 and 222 wound in opposite directions around a capstan 235 in a backend mechanism 230 as described above with reference to FIG. 2. Instrument 600 may also include a preload system 240 that is the same as preload system 240 of FIG. 2 or an alternative preload system such as described with reference to FIG. 3, 4, or 5. Instrument 600 differs from instrument 200 of FIG. 2 in the addition of take-up spring system 640 that engages tendons 221 and 222 between capstan 235 and steering section 210. Take-up system 640 in FIG. 6 includes pulleys that respectively engage tendons 221 and 222 and are spring loaded to pull on tendons in a direction perpendicular to the lengths of tendons 221 and 222. Take-up system 640 thus provides another mechanism for maintaining non-zero tension and avoiding slack in tendons 221 and 222 regardless of which direction capstan 235 turns.

Figure 7A:
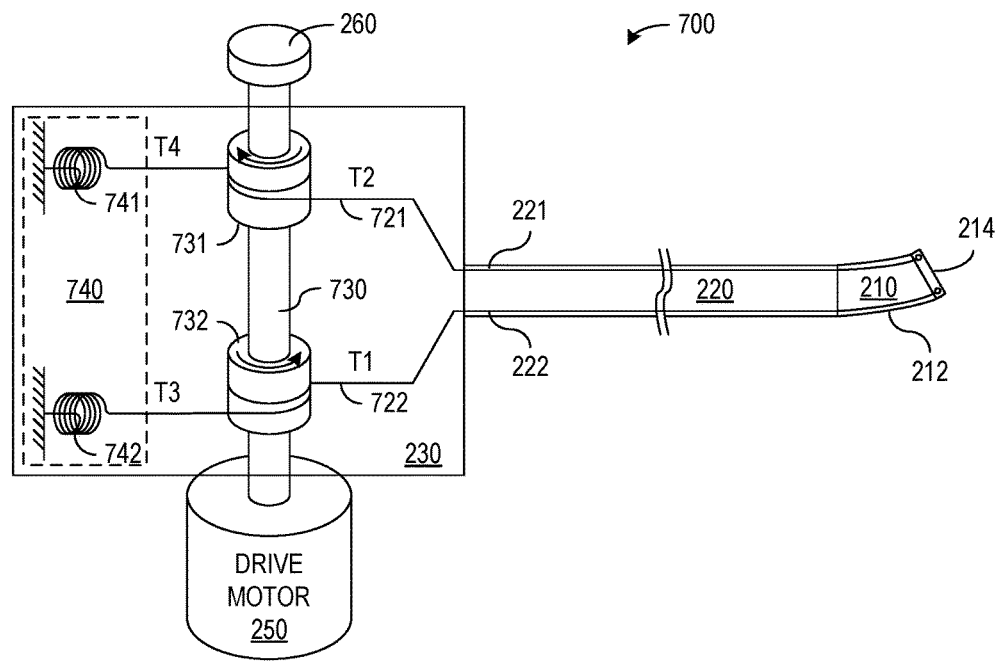
FIG. 7A shows a medical instrument with a control system using a single capstan with oppositely wound actuating tendons on two independent one-way clutches/bearings connected to independent preload systems.

The tendon 221 or 222 being fed out may need to slip on capstan 235 in order for the passive preload system to maintain at least the minimum tension at all times in the distal portions of tendons 221 and 222. In another implementation, two tendons in a self-antagonistic drive system wrap in opposite directions around two independent one-way clutches or bearings. The one-way clutches can be oriented with opposite senses, so that only one clutch engages per drive rotation direction. FIG. 7A, for example, illustrates a self-antagonistic system 700 in which two tendons 721 and 722 respectively wrap in opposite directions around respective one-way clutches or bearing 731 and 732. One-way clutch 731 is oriented so that clutch 731 pulls on the distal side tendon 721 when motor 250 or knob 260 drives a central shaft 730 clockwise, and clutch 731 slips when motor 250 or knob 260 rotates shaft 730 counterclockwise. One-way clutch 732 is oriented so that clutch 732 pulls on the distal side tendon 722 when motor 250 or knob 260 rotates shaft 730 counterclockwise and slips when motor 250 or knob 260 rotates shaft 730 clockwise. Thus, only one clutch 731 or 732 will be engaged for each drive rotation direction. A passive preload system 740 of system 700 may eliminate the chance of slack or tension build-up in tendon 721 or 722 due to the stretch of the other tendon 722 or 721 because passive preload system 740 can pull in slack on the free-wheeling clutch 721 or 722.

Figure 7B:
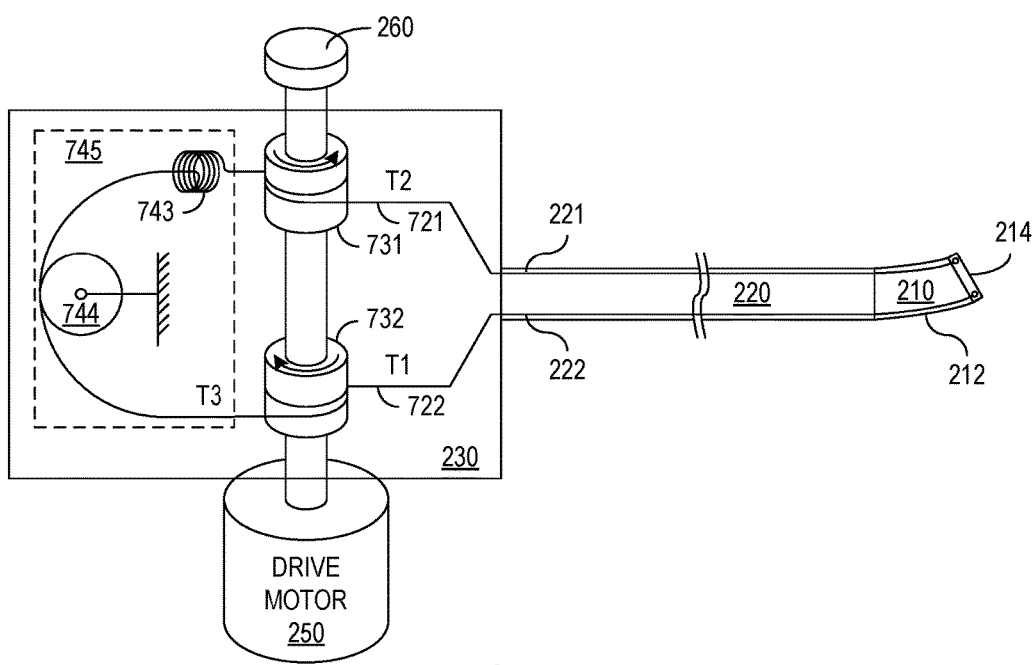
FIG. 7B shows a medical instrument with a control system using a single capstan with oppositely wound actuating tendons on two independent one-way clutches/bearings connected to a preload system including an in-line spring system and a fixed pulley.

The mechanism of the preload system 740 may be identical to the preload system 240. As shown, proximal ends of tendons 721 and 722 connect to spring systems 741 and 742 in preload system 740. Spring systems 741 and 742 maintains minimum and equal tensions in tendons 721 and 722, avoiding slack in tendons 721 and 722. Alternatively, any other preload system such as those described herein could be employed. FIG. 7B, for example, is identical to FIG. 7A except that the tendons 721 and 722 connect to a preload system 745 including an in-line spring system 743 and a fixed pulley 744 in the same manner as preload system 440 of FIG. 4.

Figure 8:
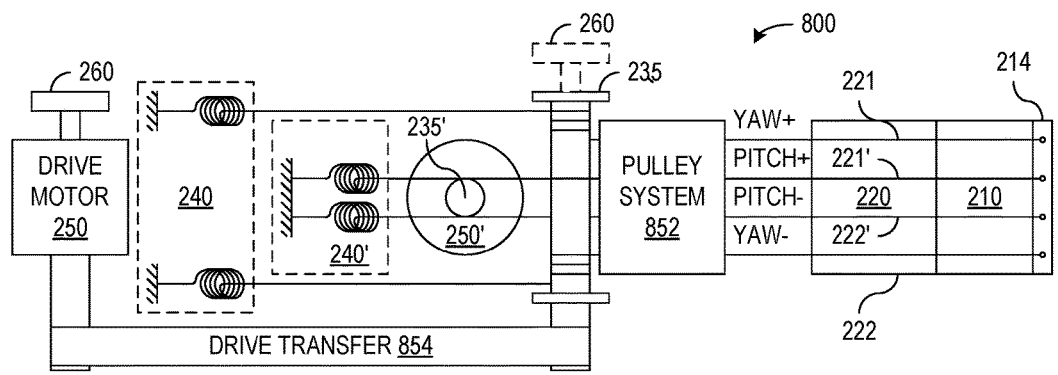
FIG. 8 shows a system for control of two degrees of freedom of a medical instrument.

Steerable instruments as mentioned above can benefit from the ability to control the pitch and the yaw of the distal tip of the instrument. FIGS. 2, 3, 4, 5, and 6 shows some examples of medical instruments in a distal tip, e.g., steering section 210, can be bent back and forth to control one angle, i.e., pitch or yaw, of the distal tip. More generally, a medical instrument could contain two such drive system for independent control of the pitch and yaw angles of the distal tip. FIG. 8, for example, illustrates a medical instrument 800 employing two pairs of actuating tendons 221 and 222 and 221' and 222' having distal ends connected to a steering section 210 of a medical device such as a steerable instrument. For example, the distal ends of tendons 221, 222, 221', and 222' may all be connected to an actuation ring 214 at 90° separations around the perimeter of ring 214. Tendons 221 and 222 wind in opposite directions around a capstan 235 that has a preload system 240 for tendons 221 and 222. Tendons 221' and 222' similarly wind in opposite directions around a capstan 235' that has a preload system 240' for tendons 221' and 222'. Pitch and yaw angles of the distal tip of instrument 800 can thus be controlled using two motors 250 or knobs 260 coupled to capstan 235 and 235'.

The separation of tendons 221 and 222 and the separation of tendons 221' and 222' at ring 214 may be perpendicular to each other for pitch and yaw actuations. As a result, associated drive systems, particularly capstans 235 and 235', may also be perpendicular to each other. The perpendicular orientations may not be the best configuration for a compact drive system for convenient handheld use of instrument 800. However, the orientation and position of drive system components such as capstans 235 and drive motors 250 can be rearranged using a pulley system 852 or a drive transfer systems 854. In particular, pulley systems 852 can be used to redirect tendons 221, 222, 221' and 222' so that capstans 235 and 235' do not need to be perpendicular. Drive transfer system 854, e.g., a belt or gear system, can similarly be used to change the position or orientation of either motor 250 relative to the capstan 235 or 235'.

Motor 250 as shown in FIG. 8 does not need to directly attach to capstan 235. More generally, a motor pack, which may include multiple drive motors, e.g., motors 250 and 250' in system 800, can connect to capstans, e.g., capstans 235 and 235', through an engagement mechanism that allows the motor pack to engage or disengage the backend mechanism including capstans of a self-antagonistic drive system. Each manual knob 260 may remain attached to the corresponding capstan 235 and apply higher tension on one of the tendon 221 or 222 to steer the instrument manually. Removal of the motor pack from the backend mechanism has advantages. In particular, the removable motor pack may be outside a sterile barrier that encloses a sterile area in which a medical procedure is performed. The motor pack may then be spared from the standard but intrusive cleaning procedures such as high pressure autoclave sterilization that may be required for the backend mechanism and the rest of the instrument. If the backend mechanism is part of a single-use instrument, the instrument can be easily replaced and recycled while the motor pack can be used again and again. The motor pack can also remain or be permanently attached to a robotically controlled arm, making the instrument smaller and lighter during manual use. For example, once a physician is done with the handheld operation of the instrument, the physician can attach the backend mechanism of the instrument onto the motor pack and robotic arm. An input device (e.g., a joystick) can then be used to control the instrument robotically.

Figure 9:
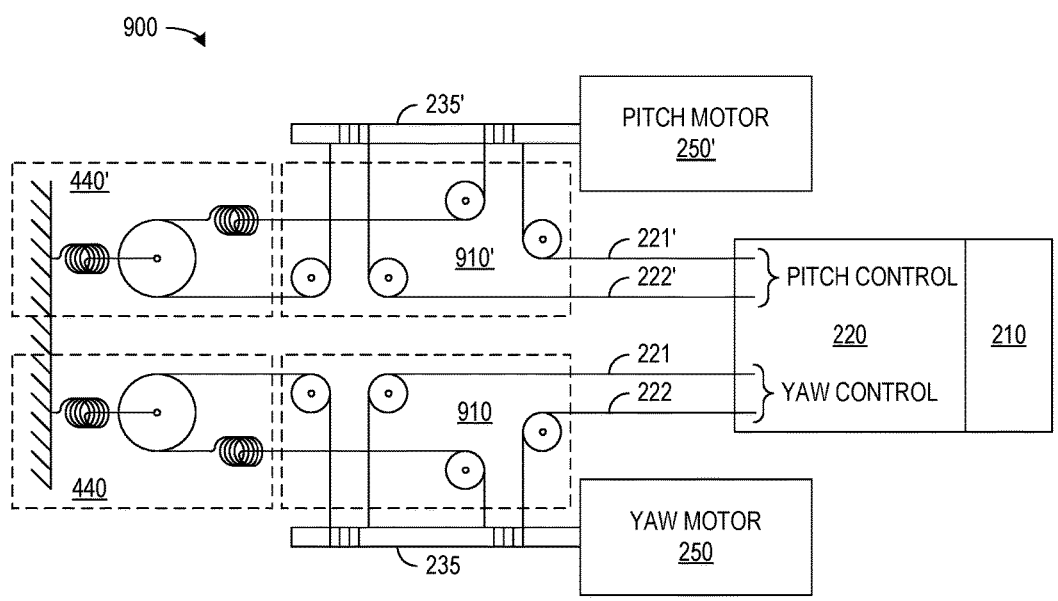
FIG. 9 is a perspective view of a backend of a catheter system with only a single capstan for each degree of freedom that is compact enough for handheld use and also capable of use with computer-aided control.

One compact or small radius configuration of a drive system for an instrument steerable in pitch and yaw directions orients rotation axes of drive motors 250 and 250' and capstans 235 and 235' along the direction of main tube 220. FIG. 9 illustrates an instrument 900 in which drive motors 250 and capstans 235 are oriented along the axis of main tube 220. Pulley systems 910 and 910' in instrument 900 can connect to respective passive preload systems 440 and 440' and change the directions of tendons 221 and 222 and tendons 221' and 222' that run along that axis through main tube 220, so that the proximal ends of tendons 221 and 222 and tendons 221' and 222' are perpendicular to the axis of main tube 220. Tendons 221 and 222 and tendons 221' and 222' can thus be wound around respective capstans 235 and 235' as described above.

One specific embodiment of instrument 900, which can provide pitch-yaw drive, can be light weight, e.g., around one pound and compact, e.g., have a maximum outside diameter less than about 60 mm. Main shaft 220 can include four tendons or pull wires, two for pitch and two for yaw, terminated at the tip of the steering section 210 at the cardinal points. Each tendon may be a pull wire in a Bowden cable with the pull wire being distally terminated on a ring in the distal steering section and proximally terminated on a preload system that allows controlled sliding. Each pull wire may include a section of a polymer cable (e.g. Kevlar) that may be routed by idlers to the motor shaft or capstan. The polymer cable portion may also wrap or wind around on motor shaft, where two sections that wind around the same motor shaft are wound in opposite directions. The preload mechanism can keep minimum tension in the pull wires at all times.

The drive systems described above can provide significant benefits for manual and computer assisted operation of an instrument. In particular, for a biopsy, a surgeon or other medical personnel may want to manually insert an instrument through a patient natural orifice such as the mouth or anus and the backend mechanisms, as described above, may be made small enough for handheld use during the insertion. One or two mechanical knobs can be provided for manual operation, allowing 2-way or 4-way, bending of a tip section of the instrument. For example, the knobs can be oriented as in a standard bronchoscope or colonoscope. The motor axis of the actuation motors can be parallel with the instrument shaft, which may leave more room near the patient's anatomy for easier manipulation. The relatively light weight and small visual mass of at least some of the drive systems described above may also be appealing or less frightening to patients undergoing a procedure such as a biopsy under conscious sedation, where the patient may be moving and aware. For computer assisted operation, drive systems can use one motor or actuator per degree of freedom, which may reduce cost and system complexity when compared to a drive system using one motor per cable.

Although particular implementations have been disclosed, these implementations are only examples and should not be taken as limitations. Various adaptations and combinations of features of the implementations disclosed are within the scope of the following claims.

What is claimed is:

1. A method for operating an instrument including an actuated structure mounted at a distal end of a shaft, the method comprising:
   rotating a capstan that is coupled to the actuated structure through a first tendon and a second tendon, the first tendon having a first portion connected to the actuated structure and extending down the shaft to the capstan, a second portion wound around the capstan in a first direction, and a third portion extending from the capstan, the second tendon having a first portion connected to the actuated structure and extending down the shaft to the capstan, a second portion wound around the capstan in a second direction that is opposite the first direction, and a third portion extending from the capstan; and
   during the rotating of the capstan, passively controlling a first tension in the third portion of the first tendon and a second tension in the third portion of the second tendon.

2. The method of claim 1, wherein the passively controlling the first tension and the second tension comprises:
   applying a force to the third portion of the first tendon; and
   applying the force to the third portion of the second tendon.

3. The method of claim 2, wherein the third portions of the first and second tendons are connected together and engaged with a pulley system.

4. The method of claim 3, wherein the applying of the force to the third portion of the first tendon comprises employing a biased spring system to attached to a pulley.

5. The method of claim 3, wherein a spring system connects the third portions of the first and second tendons together, the spring system being biased to apply the force to the third portions of the first and second tendons together.

6. The method of claim 1, wherein:
   the passively controlling of the first tension comprises keeping the first tension constant throughout a range of motion of the actuated structure; and
   the passively controlling of the second tension comprises keeping the second tension constant throughout the range of motion of the actuated structure.

7. The method of claim 1, wherein the passively controlling of the first tension comprises:
   applying a force to a proximal end of the first tendon; and
   keeping the force constant throughout a range of motion of the proximal end of the first tendon.

8. The method of claim 7, wherein applying the force comprises connecting a constant force spring to the proximal end of the first tendon, action of the constant force spring keeping the force constant over the range of motion of the proximal end of the first tendon.

9. The method of claim 1, wherein the rotating of the capstan comprises:
   rotating the capstan manually at a first time; and
   rotating the capstan using a drive motor at a second time.

10. The method of claim 9, wherein:
    the instrument is a medical instrument;
    rotating the capstan manually is performed during insertion of the instrument for a medical procedure; and
    rotating the capstan using the drive motor follows manual rotation of the capstan.

11. The method of claim 10, wherein rotating the capstan using the drive motor is during robotic operation of the instrument.

12. The method of claim 1, wherein the passively controlling of the first tension and the second tension comprises connecting a biased spring system to a slide mounting of the capstan, the slide mounting permitting the rotating of the capstan and permitting the biased spring system to linearly move the capstan.

13. The method of claim 1, wherein the passively controlling of the first tension and the second tension comprises, without need to respond to a control or feedback system, applying the first tension to the third portion of the first tendon and applying the second tension to the third portion of the second tendon.

* * * * *